United States Patent [19]

Wensky et al.

[11] Patent Number: 5,620,656

[45] Date of Patent: Apr. 15, 1997

[54] PACKAGING SYSTEMS FOR PERACID STERILIZATION PROCESSES

[75] Inventors: Afaf Wensky, Pleasanton; Phillip A. Martens, Fremont, both of Calif.; Ross A. Caputo, Long Grove, Ill.

[73] Assignee: Abtox, Inc., Mundelein, Ill.

[21] Appl. No.: 566,477

[22] Filed: Dec. 4, 1995

Related U.S. Application Data

[63] Continuation of Ser. No. 213,112, Mar. 15, 1994, abandoned, which is a continuation-in-part of Ser. No. 111,989, Aug. 25, 1993, Pat. No. 5,498,526.

[51] Int. Cl.$^6$ .............................. G01N 31/22; C12Q 1/22
[52] U.S. Cl. .................. 422/28; 422/56; 422/86; 422/87; 435/31; 436/1; 206/439; 206/459.1; 116/206
[58] Field of Search ............................... 422/27, 28, 55, 422/56, 57, 61, 86, 87, 292, 294; 435/31; 436/1; 206/459.1, 439; 116/206

[56] References Cited

U.S. PATENT DOCUMENTS

| | | | |
|---|---|---|---|
| 3,297,184 | 1/1967 | Andelin | 215/307 |
| 3,661,717 | 5/1972 | Nelson | 435/31 |
| 3,862,824 | 1/1975 | Chapman . | |
| 4,091,921 | 5/1978 | Lewis . | |
| 4,098,577 | 7/1978 | Halpern | 436/1 |
| 4,145,186 | 3/1979 | Anderson | 422/57 |
| 4,168,779 | 9/1979 | Yokokoji et al. | 206/439 |
| 4,188,437 | 2/1980 | Rohowetz . | |
| 4,206,844 | 6/1980 | Thukamoto et al. | 206/439 |
| 4,240,926 | 12/1980 | McNeely | 106/20 R |
| 4,304,869 | 12/1981 | Dyke | 435/296 |
| 4,328,182 | 5/1982 | Blake | 422/56 |
| 4,416,984 | 11/1983 | Wheeler, Jr. | 435/31 |
| 4,461,837 | 7/1984 | Karle et al. | 435/296 |
| 4,579,823 | 4/1986 | Ryder | 435/296 |
| 4,580,682 | 4/1986 | Gorski et al. | 206/569 |
| 4,596,773 | 6/1986 | Wheeler, Jr. | 435/31 |
| 4,671,936 | 6/1987 | Barron | 422/59 |
| 4,717,661 | 1/1988 | McCormick et al. | 435/31 |
| 4,732,850 | 3/1988 | Brown et al. | 435/31 |

(List continued on next page.)

FOREIGN PATENT DOCUMENTS

| | | |
|---|---|---|
| 0014447 | 8/1980 | European Pat. Off. . |
| 0069037 | 1/1983 | European Pat. Off. . |
| 2027604 | 5/1979 | Germany . |
| 90140189 | 1/1989 | Germany . |
| 273776A1 | 11/1989 | Germany . |
| 1531606 | 8/1976 | United Kingdom . |
| 93/24152 | 12/1993 | WIPO . |
| 95/06134 | 3/1995 | WIPO . |

OTHER PUBLICATIONS

"Guidance on Premarket Notification [510(k)] Submission for Sterilizers Intended for Use in Health Care Facilities," Infection Control Devices Branch, Div. General & Restorative Devices of the Food and Drug Administration, Mar. 1993.

"Biological and Chemical Indicators," HIMA Report 78–4.4, a Medical Device Sterilization Monographs published by the Health Industry Manufactures Association, Aug. 1978.

(List continued on next page.)

Primary Examiner—Robert J. Warden
Assistant Examiner—E. Leigh Dawson
Attorney, Agent, or Firm—Majestic, Parsons, Siebert & Hsue

[57] ABSTRACT

Devices useful to monitor whether or not an article has been exposed to sterilizing conditions are provided and comprise a package and an indicator associated with the package. The package is sufficiently permeable to admit sterilizing gas or vapor into the package. The indicator associated with the package changes color from a first color (indicating ambient conditions) to a second color (indicating exposure to acidic gas or vapor). Both the first and second colors of the indicator are stable and preferably substantially maintain their colors under ambient conditions. Particularly, preferred embodiments are adapted for use with peracetic acid sterilization processes.

21 Claims, 2 Drawing Sheets

U.S. PATENT DOCUMENTS

| | | | |
|---|---|---|---|
| 4,741,437 | 5/1988 | Gorski et al. | 206/22 |
| 4,743,537 | 5/1988 | McCormick et al. | 435/296 |
| 4,828,797 | 5/1989 | Zwarun et al. | 422/55 |
| 4,839,291 | 6/1989 | Welsh et al. | 435/296 |
| 4,883,641 | 11/1989 | Wicks et al. | 422/50 |
| 4,885,253 | 12/1989 | Kralovic | 435/296 |
| 4,914,034 | 4/1990 | Welsh et al. | 435/296 |
| 4,935,371 | 6/1990 | Rickloff | 435/296 |
| 5,066,464 | 11/1991 | Augurt | 422/58 |
| 5,073,488 | 12/1991 | Matner et al. | 435/31 |
| 5,084,239 | 1/1992 | Moulton et al. | 422/22 |
| 5,167,923 | 12/1992 | Van Iperen | 422/58 |
| 5,260,023 | 11/1993 | Evans, II | 422/40 |
| 5,344,017 | 9/1994 | Wittrock | 206/459.1 |
| 5,377,496 | 1/1995 | Otto et al. | 116/206 X |

OTHER PUBLICATIONS

Reich et al., "Accelerated Aging of Packaging: Considerations, Suggestions, and Use in Expiration Date Verification," *Sterilization Science, MD&DI*, Mar. 1988.

3M Health Care Product Literature on "3M Autoclave Tape," Infox™, and Comply™ sterilization indicator tape, strips, and load record cards, undated.

Propper Product Literature on "Gas–Chex®,"Steri–Dot™, OK®, Strate–Line™, and Propper Blue Autoclave Indicator Tape indicator strips, dots, and tape, 1986.

North American Science Associates, Incorporated product Literature on "NAmSA® Chemical Indicators," undated.

ATI Product Literature on "EO Sterilization Indicators," Sterilometer® Steam strip, Dry Heat Indicator Labels, Sterilabel® Indicator Labels, Sterilizer Record Cards, Header Peel Dust Covers—Self–Seal, Sterilization Tapes, May 1989, Dec. 1990, and undated.

Castle Product Literature on "Steam Monitor Strips" and EO Monitor Strips, undated.

Premarket Notification Letter to the Food and Drug Administration, Jul. 10, 1992.

Davenport Journal of Parenteral Science & Technology vol. 43 No. 4 pp. 158–165 (1989).

PACKAGING SYSTEMS FOR PERACID STERILIZATION PROCESSES

This application is a continuation of Ser. No. 08/213,112, filed Mar. 15, 1994, now abondoned, which was a continuation-in-part of Ser. No. 08/111,989, filed Aug. 25, 1993, of common assignment herewith, and now U.S. Pat. No. 5,498,526.

FIELD OF THE INVENTION

The present invention generally relates to sterilization process packaging with components such as chemical indicators, which are useful in indicating that medical devices or apparatus have been exposed to one or more sterilization process conditions, and more particularly relates to devices useful to indicate sterilization cycle exposure when the sterilization cycle includes use of an acidic gas or vapor such as peracetic acid.

BACKGROUND OF THE INVENTION

Chemical indicators are generally used to monitor whether or not an article, such as medical apparatus, has been exposed to sterilizing conditions. The type of chemical indicator discussed here is commonly known as a "throughput indicator." This type of indicator responds to one or more physical or chemical components in the sterilization environment, but it does not necessarily have to respond to all the components necessary for sterilization. Since the indicator response may occur in the absence of one or more essential sterilization components, the indicator response is not necessarily an indication of sterility. The chemical indicator only indicates that it and the accompanying articles have been processed in a sterilizer.

Often, the indicator takes the form of a reactive chemical which reacts with a chemical in the sterilizing environment to form a new chemical with different properties, frequently a different color. Other indicators react to physical conditions encountered during sterilization; for instance, wax indicators melt when exposed to the high temperatures encountered during autoclaving. Descriptions of various chemical indicators may be found in the monograph "Biological and Chemical Indicators," Report 78-4.4 of the Health Industry Manufacturer's Association (HIMA).

Among the important performance characteristics for chemical indicators are readability, reliability, selectivity, stability, and safety. "Readability" refers to the indicator characteristics which allow users to differentiate between unexposed indicators and those which have been exposed to sterilization conditions. "Good readability" means that virtually all healthcare workers, including those with common vision problems such as color blindness, can distinguish exposed indicators from unexposed indicators. For example, readability may be difficult when a user attempts to determine the shade of a color such as light brown turning to medium brown as the color change. Further, indicators should change in contrast as well as color. An indicator which changed, for example, from red to green, could pose problems for users with color vision defects unless there was an accompanying (sufficient) contrast change.

Stability is also an important characteristic. The indicating means of both unexposed and exposed indicators must not change under the normal storage conditions the article encounters. One type of commercially available chemical indicator, for example, must be stored in a refrigerator to prevent incorrect color changes over normal storage, which is inconvenient and disadvantageous.

Chemical indicators have been developed and are used with both of the prevalent sterilization processes: steam and ethylene oxide. For example, U.S. Pat. No. 4,914,034, issued Apr. 3, 1990, inventors Welsh and Dyke, describes disposable test packs for monitoring steam and ethylene oxide sterilization cycles, which include a chemical process indicator strip. U.S. Pat. No. 4,671,936, issued Jun. 9, 1987, inventor Barron, describes a cation exchange resin for monitoring alkylene oxide cycles (e.g. ethylene oxide).

Recently, a process for sterilization that includes exposing an article in a sterilizing chamber under reduced pressure to at least one exposure cycle of a peracid antimicrobial agent has been described by U.S. Pat. No. 5,084,239, issued Jan. 28, 1992, inventors Moulton et al. This sterilization process holds promise as replacement for the presently used ethylene oxide sterilization processes, which are being subjected to increasing scrutiny and safety concerns because ethylene oxide is a carcinogen, and as an alternative to conventional steam sterilization also. Although steam sterilization processes are effective for medical devices such as metal implements, the elevated temperatures to which articles are exposed during steam processing do not permit sterilization of many synthetic (especially plastic) materials or devices packaged in temperature sensitive wraps.

Accordingly, there is a need for suitable chemical indicators for monitoring exposure to a sterilization process where the sterilization cycle includes an acidic gas or vapor, particularly when the cycle is conducted under reduced pressure.

SUMMARY OF THE INVENTION

In one aspect of this invention, a device useful to monitor whether or not an article, such as medical apparatus, has been exposed to sterilizing conditions comprises a package and an indicator associated with the package. The package has at least a portion that is sufficiently permeable to admit a sterilizing amount of gas or vapor into the package when it is sealed (such as sealed to enclose the article being sterilized). However, the package substantially bacterial impermeable when sealed.

The indicator associated with the package changes color from a first color to a second color in response to acidic gas or vapor exposure. Both the first and second colors of this indicator are substantially stable. Preferred embodiments of the invention include indicators that substantially maintain their colors under ambient conditions for at least about one year.

DETAILED DESCRIPTION OF THE PREFERRED EMBODIMENTS

Devices in accordance with this invention are useful to indicate sterilization cycle exposure of an article (such as medical apparatus) when the sterilization cycle includes an acidic fluid, typically a gas or vapor. Among the inventive device embodiments of this invention are those comprising a package and one or more indicators associated with the package. One indicator component of the inventive packaging system is of the chemical indicator type.

Figure 1:
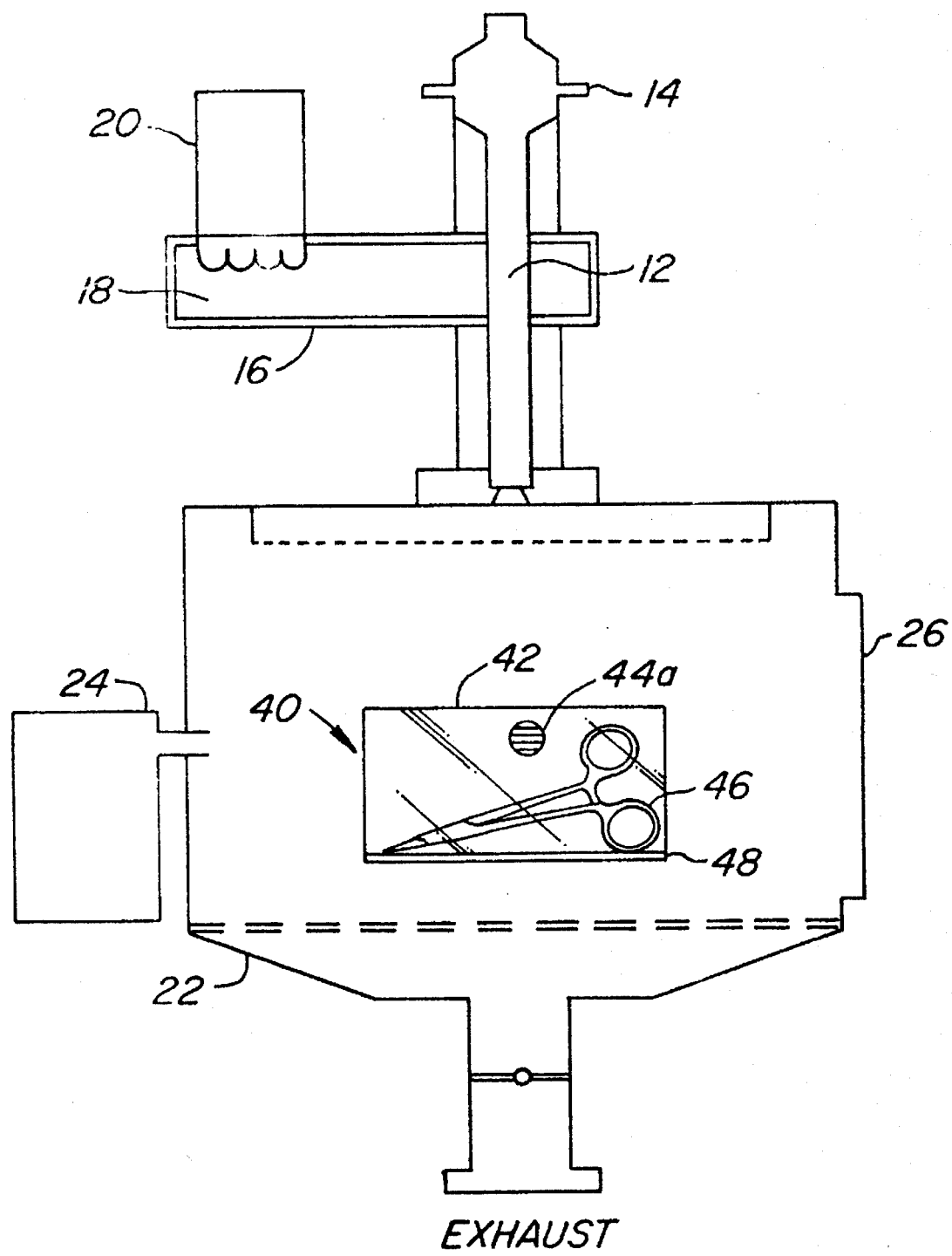
FIG. 1 illustrates a schematic cross-section of a sterilizing apparatus with a plane view of an inventive embodiment within the schematically represented sterilizing apparatus before use of the apparatus to sterilize.

Turning to FIG. 1, a sterilizing apparatus 10 with which the invention is useful may comprise, for example, a plasma chamber 12, a sterilization chamber 22, and access into chamber 22, such as door 26. Means for generating the plasma may include waveguide assembly 16, microwave 18, and magnetron 20 which generate plasma upstream of sterilization chamber 22 from a suitable gas mixture introduced at inlet 14. For example, within plasma chamber 12, gas is energized by microwave radiation and forms a plasma having an initial high concentration of ions and ultraviolet emissions. By the time the plasma enters the sterilization chamber 22, the plasma's active downstream product consists essentially of highly reactive uncharged atoms and free radicals and uncharged electronically excited molecules. In addition, another inlet 24 may deliver an additional sterilizing species during a separate cycle, such as an antimicrobial fluid.

An inventive embodiment 40 of the invention comprises a package, or pouch, 42 sealed along one edge 48 with a medical device for sterilization (here, illustrated as forceps 46) within pouch 42. An indicator 44 is associated with the pouch and adapted to be visually observed.

Figure 2:
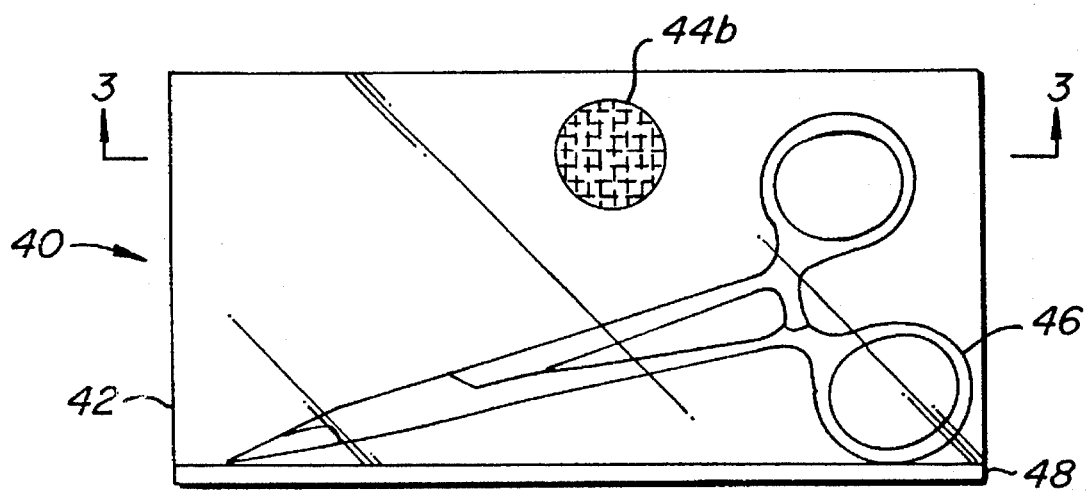
FIG. 2 is a cut-away of the inventive embodiment as in FIG. 1, but following use of the sterilizing apparatus to expose the inventive embodiment to sterilizing conditions.

As shown by FIG. 1, the indicator has first color (illustrated as 44a, lined to indicate a blue color). With reference to FIG. 2, one sees the indicator (here illustrated after exposure to a sterilization cycle and thus designed 44b), with a changed color lined to indicate a yellow color. That is, the chemical indicator 44 associated with the package 42 visually indicates whether exposure to an acidic fluid of a sterilization cycle has occurred by changing color from a first color (44a of FIG. 1) to a second color (44b of FIG. 2) in response to acidic gas or vapor exposure. By "acidic" is meant "capable of causing an indicator in the basic form to turn to the acidic form." Thus, use of the term "acidic" is not limited to a pH less than 7, since an indicator with a $pK_a$ of 11 would turn from its basic form to its acidic form if exposed to a pH of lower than about 10.5. The manner of association of the indicator with the package can take various forms, which will be described hereinafter.

Packages of the invention have at least a portion that is gas or vapor permeable, but bacteria impermeable. The gas or vapor permeable portion is configured so as to define at least one path for providing entry of sterilizing gas into contact with the article to be sterilized. By "sterilizing gas" we mean an acidic fluid, preferably in gaseous or vapor form. The words "gas" and "vapor" are used throughout as being substantially synonymous, but embodiments of the invention are particularly useful to indicate exposure to an antimicrobial fluid (e.g. peracid vapor), such as peracetic acid that vaporizes from solution due to reduced sterilizing chamber pressure and/or heating.

The permeable package portion may constitute the entire package, but frequently the package will be constructed of the permeable portion and one or more other materials. The other material(s), when present, are usually gas and bacteria impermeable.

The portion that is permeable to gas or vapor, but impermeable to bacteria, will typically be microporous with the volume average diameter of pores being in the range of from about 0.02 to about 0.5 µm. Suitable microporous materials include spunbonded polyethylene, spunbonded polypropylene, microporous polyethylene, and microporous polypropylene, usually in the form of film or sheet. Paper can also be used as the permeable portion for inventive embodiments. The thickness of the permeable material can vary, but usually will be in the range of from about 0.23 to about 0.65 mm.

Examples of impermeable materials suitable in forming part of the inventive packages include polyester, polyethylene, polypropylene, poly(vinyl chloride), and poly(ethylene terephthalate), usually in the form of film, sheet, or tube. Typically the impermeable materials will also be sufficiently transparent or translucent as to permit visual observation into the package from a position exterior to the package when the package is sealed. This visual observation into the package is important for one embodiment of the invention wherein an indicator, or dye composition, is adapted to be sealed within the package and to be visually observed therein.

Packages of the invention can be formed with seams, joints, and seals made by conventional techniques, such as, for example, heat sealing and adhesive bonding. Examples of heat sealing include sealing through use of heated rollers, sealing through use of heated bars, radio frequency sealing, and ultrasonic sealing. Peelable seals based on pressure sensitive adhesives may also be used.

The package prevents contamination after sterilization for an enclosed article (such as medical apparatus) and any additionally enclosed, optional components during shelf life until use. Microorganisms external to the package are prevented entry by the packaging barrier.

The inventive embodiments were developed for preferred use with a particular gas sterilization process. However, some embodiments of the invention are broadly useful with other acidic sterilants and other acidic sterilizing processes.

In the first step of the particular process for which the invention was developed, a gas, typically a peracid, such as peracetic acid vapor, is introduced as a sterilant. U.S. Pat. Nos. 5,084,239 and 5,244,629 describe this sterilizing process, in which one step, or sterilizing cycle, can utilize peracid vapor, such as peracetic acid, as sterilant. These patents are hereby incorporated herein by reference.

The term "peracid" as used herein, is defined to include well known peracid antimicrobial agents, such as saturated and unsaturated peralkanoic acids including peraralkanoic acids having from one to eight carbon atoms and halogenated derivatives thereof. The halogenated peracids contain one or more chloro, bromo, iodo, or fluoro groups. Examples of suitable peracids include peracetic acid, halogenated peracetic acids, performic acid, perpropionic acid, halogenated perpropionic acids, perbutanoic acid and its halogen derivatives, percapronic acid and its halogen derivatives, percrotonic acid, monopersuccinic acid, monoperglutaric acid, and perbenzoic acid, for example. The preferred peracids are sufficiently volatile to form an effective sporicidal vapor concentration at temperatures of less than 80° C.

Peracid sterilization is effected by contact of the article with antimicrobial concentrations of the peracid vapor. A pulsed peracid treatment may be carried out by exposing the article to be sterilized to peracid vapor having a concentration of from 1 to 35% (w/w) peracid, and more preferably from 5 to 12% (w/w) peracid, for a time sufficient to permit contact of the vapor with all surfaces of the article being sterilized. More than one such exposure, or pulsed period, may be used. The pulsed contact exposure time is preferably from about 10 to about 20 minutes per pulsed period with packaged articles. Six such periods, for a total exposure of about two hours, are particularly preferred. The peracid exposure can be carried out at a temperature of from 20° to 80° C., and preferably from 40° to 60° C.

Some peracids in certain concentrations are explosive at elevated temperatures. For this reason, peracetic acid is usually transported and stored in aqueous solutions having less than 35 wt. % peracetic acid. The peracetic acid solution is easily vaporized, and effective treatment of articles, according to this invention, can be achieved by exposing the articles to peracetic acid vapors at reduced chamber pressures, such as in the range of from about 1 to about 30 torr. The lower pressure limit is the lower range limit of the effective concentration of the peracetic acid necessary for reasonably short processing times.

Thus, the article being sterilized is preferably exposed to gaseous antimicrobial agent at partial pressures of from about 4 to 50 torr and a treatment time of at least about 5 minutes, preferably about 10 to 15 minutes. The gas mixture with antimicrobial agent is removed by evacuating the sterilizing chamber to less than about 4 torr. In between pulses of antimicrobial fluid exposure one may, for example, treat with plasma at reduced sterilization chamber pressures, typically on the order of 0.1 torr to 10 torr.

Embodiments of the invention include chemical indicators that change color from a first color to a second color in response to the just described acidic gas or vapor exposure. The first color is that which is observable when the indicator has not been exposed to acidic gas or vapor, but rather is the color at normal, ambient conditions (that is, the first color is the basic form of the pH sensitive dye). It is believed that particularly preferred indicators of this invention, as below further described and exemplified, actually respond to acetic acid vapor, which is a component of vaporized peracetic acid solution, and can also be formed by the breakdown of peracetic acid.

Preferred embodiments of the invention are sufficiently selective, or sensitive, so as to change from the first color to the second color when exposed to sufficient concentration of the acid gas or vapor within a practical time or exposure. For example, a solution of 10% peracetic acid and 11% acetic acid can provide a concentration of about 2.2 mg/l acetic acid vapor, which causes chemical indicator embodiments prepared as hereinafter described by Example 1 to change color after about a 15 minute exposure while another formulation (5% peracetic acid and 11% acetic acid) can provide a concentration of about 1.75 mg/l of acetic acid vapor to cause the indicator to change color within about 20 minutes.

Once the packaged article is removed from the sterilization process, then the indicator, or dye composition, maintains the second color and is substantially stable under normal storage conditions (typically ambient conditions). Both unexposed and exposed indicator colors should be stable. Preferred embodiments of the present invention include indicators that substantially and stably maintain their colors under ambient conditions for at least about one year. If an unexposed indicator were to change color to that of an exposed indicator as the result of storage, an unsterilized device might be used on a patient. This could be disastrous.

Figure 3:
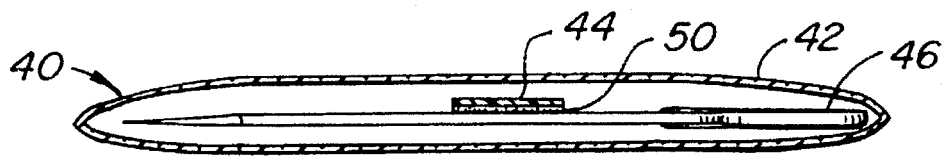
FIG. 3 is a cross-sectional view taken along lines 3—3 of FIG. 2.

In one chemical indicator embodiment, the indicator includes a substrate and a dye composition. Referring to FIG. 3, indicator 44 is constituted by a dye composition carried on substrate 50. The dye composition is preferably absorbed on substrate 50, and the substrate is of a size to be sealed within the package and visually observed from a position outside the package. Suitable substrates include, for example, filter paper or acid-free blotter paper.

Figure 4:
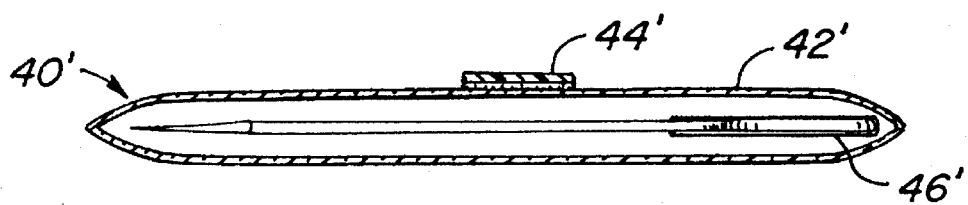
FIG. 4 is similar to FIG. 3, but of another embodiment of the invention.

Turning to FIG. 4, indicator 44' differs from the FIG. 3 embodiment by being carried on a wall of pouch 42' itself. In this second embodiment, the chemical indicator again includes the dye composition, but this dye composition can be carried by the package itself, such as by being imprinted on an exterior (or interior, if visible), surface.

In yet another embodiment of the chemical indicator (not illustrated), an elongated, flexible member, or substrate, has an adhesive layer on one side and the dye composition on the other side. This embodiment can then be affixed to the package either as a label and/or to hold the package or wrappings in place, and is especially useful for large loads wrapped in muslin or synthetic sheets. Often large sterilizer loads, such as trays of instruments, are packaged in sheets of muslin or sheets of porous synthetic fabrics. Two or more layers of wrapping are typically used. These layers of material act as biocontamination barriers. The sheets are typically held in place with tape, and the embodiment of the invention as just described is useful to hold the wrappings together as a biocontamination barrier in lieu of conventional tape.

Dye compositions for the inventive embodiments include a pH sensitive dye where the dye gives a color change, preferably at a pH approximately the same as or higher than the pK of the acidic fluid selected as the sterilant (or as a component in the sterilant gas or vapor) in the sterilization cycle being monitored. For example, although the pK of peracetic acid is about 9, the pK of acetic acid is about 4.75. Thus, the dyes for use with a peracetic acid exposure should change color at about 9 or at about 4.75 pH.

Among the preferred suitable pH sensitive dyes for practicing this invention are 3', 3", 5', 5"-tetrabromophenolsulfonephthalein (Bromophenol Blue) and 3',3",5',5"-tetrabromo-m-cresolsulfonephthalein(Bromocresol Green). Bromophenol Blue is blue at a pH of about 4.6, and turns yellow in the pH range between about 3 to 4.6. Bromocresol Green is blue at about pH 5.4, and turns yellow in the pH range between about 3.8 and 5.4. Both of these preferred dyes have been determined to be stable so as to maintain their colors (first and second colors, respectively) under ambient conditions for at least about one year.

Dye compositions of the invention preferably include one or more conventional pH adjusting agents, binding agents, and/or thickening agents. The pH adjusting agents are useful to place the dye composition near or at the point where color change begins to occur. The binding and/or thickening agents may be selected from a wide range of binding and thickening agents known to the art, and are chosen so that they do not interfere with the dye activity.

The binding and/or thickening agents, if present, can be used to adapt the dye composition for the selected manner by which it will be associated with packaging, substrate, or flexible member, as the case may be. For example, when the dye composition is absorbed on a substrate such as filter paper or acid-free blotter paper, then glycerol is a useful thickening agent, as well as silica and bentonite.

Device embodiments of the invention comprising packaging and an associated chemical indicator may include additional components (not illustrated). Particularly preferred embodiments are packaging systems that include biological indicators as well as chemical indicators. The biological indicators are for monitoring exposure to a sterilizing process where a selected number of viable organism spores are inoculated on a carrier and included in pouch 42 or 42'.

Spores, rather than the vegetative form of an organism in biological indicators, are used because vegetative bacteria are known to be easily killed by sterilizing processes. Spores also have superior storage characteristics as they can remain in their dormant state for years. Thus, when sterilization of a standardized spore strain occurs from a sterilization process, such can provide a high degree of confidence that sterilization of bacterial strains in the sterilizing chamber has occurred. We particularly prefer use of *Bacillus circulans* spores, which can be on a carrier placed within the sealed package to maintain integrity of the spores until the biological indicator is used for its intended purpose.

*Bacillus circulans* is preferred because the organism is considered non-pathogenic, is stable enough to provide a relatively long shelf life when packaged, is easy to grow so that sterility tests can be performed using common techniques and materials, and has been found to have a high resistance and more stable resistant pattern when compared to prior art organisms such as *B. subtilis* and *B. stearothermophilus*, as exemplified by Ser. No. 08/111,989, filed Aug. 25, 1993.

*Bacillus circulans* cultures are available, for example, from the American Type Culture Collection, 12301 Parklawn Drive, Rockville, Md. 20852. Among the *B. circulans* strains available are ATCC 61, ATCC 13403, and ATCC 21821, 21822 (subspecies *n. proteophilus* and *n. biotinicus*, respectively).

When biological indicators are included they can be either simply enclosed within the package or pouch 42, 42' or they can have their own package before they are placed within the outer package for the assemblage.

It has been suggested that the type of product or carrier material inoculated can significantly affect the resistance of the biological indicator. Filter paper carrier material has been shown to have excellent storage stability. Preferred carriers are formed of materials such as filter paper, which can be readily macerated along with the carried spores if one wishes to perform survivor determinations.

The carrier, such as a filter paper carrier, can be quite simply inoculated with spores by preparing an aqueous suspension with the desired spore concentration and pipetting aliquots onto the carrier. Thus, inoculation of carrier can be performed according to the USP XXII Bacteriostasis Test Method. Briefly, a suspension of *Bacillus circulans* spores in water is prepared so as to yield a desired number of spores per aliquot for inoculating a carrier such as filter paper.

The *Bacillus circulans* spores may be placed into the package as a selected number as follows. Before inoculating spores onto the carrier, a heat shock step is desirably performed. Heat shock is a sublethal thermal treatment given to spores to prepare the enzymatic reactions for germination. Thus, a preferred sequence is a heat shock step, cooling, diluting the spore suspension, and then inoculating carriers and drying.

The following method can be used to prepare inoculated carriers and to perform a population count. An inoculated paper carrier is placed into a test tube containing 10 ml of water and several small glass beads. The tube is agitated vigorously until the paper is macerated by the action of the glass beads. This can be accomplished by means of a vortex mixer. The macerated mixture is diluted using ordinary serial dilution techniques, and aliquots of the dilutions are transferred to petri plates. An agar solution containing growth medium, such as Tryptic Soy Agar, is prepared, sterilized by autoclaving, and kept in liquid form by maintaining its temperature at about 60° C. The agar is added to the petri plates in a quantity sufficient to fill the plates to a depth of at least 5 mm. The agar is mixed with the spore aliquots by gentle agitation. The mixture is allowed to stand, and the agar gels as the solution cools. The plates are then inverted and incubated at 32°–37° C. for 24–48 hours. Plates with 30–300 calories are enumerated, and the average population per carrier is calculated.

As earlier noted, the biological indicator itself may be separately packaged to facilitate test uses, storage, or record keeping separate from the chemical indicator or other components.

Without intending to limit the invention, aspects of the invention will now be exemplified by the following examples.

EXAMPLE 1

Chemical indicator embodiments of the invention were prepared by admixing the following components:

0.4 gm/l dye (Bromophenol Blue, 0.1 g in 14.9 ml 0.01N NaOH plus 235.1 ml water)

3.0 gm/l pH adjusting agent (0.01N acetic acid, sufficient to adjust to pH 6.5)

4.0 gm/l thickener/binder (2.5 gm/l silica and 1.5 gm/l bentonite)

The just described dye composition was applied to substrate by placing a coil of Whatman 3MMCHR chromatography paper, in a beaker of the dye composition and leaving it in the beaker for a minute. The paper was then removed, drained, dried, and cut into pieces. The indicators were then individually sealed in Tyvek/Mylar pouches (commercially available as Tower Plasti-Peel pouches) and the package edges were sealed by heating. The just described embodiments of the invention are illustrated by FIGS. 2 and 3 (but without the forceps of those illustrations).

EXAMPLE 2

Pouches as prepared in Example 1 were exposed to complete sterilization or partial sterilization processes. The peracetic acid formulation used a solution of 10% peracetic acid, 11% acetic acid, 2% $H_2O_2$, less than 1% nonvolatile substances, and the balance water.

Complete Sterilization Process: the indicators were exposed to six treatments, with each treatment consisting of a 20 minute exposure to the peracetic acid vapor portion (concentration of about 2.2 mg/l acetic acid vapor) of the process followed by a 10 minute exposure to the plasma portion of the process.

One Sixth Sterilization Process: the indicators were exposed to one treatment consisting of 20 minute exposure to the peracetic acid followed by a 10' plasma treatment.

Partial (15') peracetic acid Treatment: the indicators were exposed to 15' treatment of peracetic acid vapor.

Partial (10') peracetic acid Treatment: the indicators were exposed to 10' peracetic acid vapor.

Exposure to the complete sterilization process caused the indicators to turn from dark blue to light yellow (which represents not only a color change but also a contrast change). The color of the exposed indicators shifted slightly toward green after one day. However, there was still an unmistakable color difference between exposed and unexposed indicators.

Exposure to the ⅙ process caused the indicators to show a color change very similar to the full cycle immediately after exposure. This color also shifted slightly toward greenish yellow after 24 hours.

Exposure to the peracetic acid phase of the sterilization process for 15 minutes also caused the indicators to turn from dark blue to light yellow. After 24 hours the color was light greenish yellow.

Exposure to the peracetic acid phase of the sterilization process for 10 minutes also caused the indicators to turn from dark blue to yellow. This yellow color also toward greenish yellow after a few hours. After 24 hours, the indicators had a blue-green color.

The color change from yellow to greenish yellow upon standing was attributed to a gradual absorption of moisture which raises the pH slightly. In all cases, there was an obvious difference between the appearance of exposed and unexposed indicators at all the exposure times tested.

Another peracetic acid formulation was tested (5% peracetic acid, 11% acetic acid, 22% $H_2O_2$, less than 1% nonvolatile stabilizer, and the balance $H_2O$), which provided 1.75 mg/l of acetic acid vapor, and caused the indicators to change color within 20 minutes of exposure in a manner similar to the just described protocol and results with the 10% peracetic acid formulation.

EXAMPLE 3

This study determined whether any visual changes occurred in the indicators prepared as described by Example 1 after treatment with accelerated aging conditions, which were designed to simulate one year of shelf life, and after exposing these indicators to a sterilization cycle.

Aging was done under the following set of accelerated aging conditions:

First: 55°±5° C., 70%–80% relative humidity, 12 days

Followed by: 55°±5° C., no more than 20% relative humidity, 12 days

Followed by: −10° to 20° C. 2 days

The fresh indicators that were exposed to a sterilization cycle changed color from dark blue to light yellow and remained yellow 24 hours after exposure. Unexposed indicators that were treated with a three-step accelerated aging conditions had the same dark blue color as untreated indicators. After exposing these indicators to a sterilization cycle, the color changed from dark blue to light yellow as with indicators that were not aged. The color remained yellow 24 hours after exposure. Real time aging studies (that have been running concurrently to date) confirm the results obtained with the accelerated aging studies.

Thus, chemical indicators of the invention are characterized by good readability, reliability, and stability, and are suitable for monitoring exposure to a sterilization process where the sterilization cycle includes an acid gas or vapor, such as peracetic acid with an acetic acid component, particularly when the cycle is conducted under reduced pressure.

It is to be understood that while the invention has been described above in conjunction with preferred specific embodiments, the description and examples are intended to illustrate and not limit the scope of the invention, which is defined by the scope of the appended claims.

It is claimed:

1. A device useful to indicate sterilization cycle exposure of an article when the sterilization cycle includes an acidic gas or vapor, comprising:

a package capable of sealingly enclosing an article, the package having at least a portion with sufficient permeability to admit a sterilizing gas or vapor into contact with the article when sealingly enclosed within the package, the package being substantially bacteria impermeable when sealed; and, an indicator associated with the package and adapted to be visually observed therewith, the indicator including a pH sensitive dye and a pH adjusting agent, the indicator having a first color under ambient conditions and adapted to change color from the first color to a second color in response to acidic gas or vapor exposure, the pH adjusting agent effective to place the pH of the indicator to an acidic point about where color change from the first color to the second color begins to occur, wherein said indicator is adapted to substantially maintain the first color under ambient conditions in the absence of exposure to a sterilization cycle and to substantially maintain the second color after acidic gas or vapor exposure is terminated.

2. The device as in claim 1 wherein the permeable package portion admits peracid and/or acetic acid vapor at reduced pressure.

3. The device as in claim 2 wherein the package permits visual observation into the package and the indicator is adapted to be sealingly enclosed within the package.

4. The device as in claim 3 wherein the permeable package portion begins to admit vapor in less than about five minutes after package exposure thereto.

5. The device as in claim 2 wherein the pH adjusting agent of the indicator is acidic.

6. The device as in claim 2 wherein the indicator includes a substrate and a dye composition, the dye composition being absorbed on the substrate and having a pH adjusted by the pH adjusting agent to between about 4.6 to about 6.5.

7. The device as in claim 6 wherein the dye composition includes Bromophenol Blue.

8. The device as in claim 1 wherein the package is adapted sealingly to enclose an article and the indicator by heat sealing or adhesive bonding.

9. A package for articles to be sterilized by a sterilization cycle including exposure to an acidic fluid, comprising:

a package portion having sufficient permeability to admit a sterilizing amount of gas or vapor into the package when an article to be sterilized is enclosed therein, the package being sealable and substantially bacteria impermeable after sealing; and, a dye composition adapted to be stably carried by the package and visually observable from a position exterior to the package when sealed, the dye composition being substantially stable and capable of visually indicating whether exposure to an acidic fluid of a sterilization cycle has occurred, the dye composition including a pH sensitive dye and a pH adjusting agent, the pH sensitive dye giving a substantially stable color change in response to acetic fluid exposure, the pH adjusting agent adjusting the pH of the dye composition to between about 4.6 to about 6.5.

10. The package as in claim 9 wherein the acidic fluid includes peracid and/or acetic acid vapor.

11. The package as in claim 10 wherein the pH sensitive dye changes color at a pH of about 4.6.

12. The package as in claim 9 further comprising:

a biological indicator.

13. The package as in claim 12 wherein the biological indicator includes a selected number of viable organism spores and a carrier being inoculated with the spores.

14. The package as in claim 13 wherein the organism includes *Bacillus circulans*.

15. The package as in claim 9 or 12 wherein the dye composition includes Bromophenol Blue or Bromocresol Green.

16. The package as in claim 9 or 12 wherein the dye composition is affixed to a package surface.

17. A packaging system for monitoring exposure to a sterilizing process, comprising:

a selected number of viable organism spores, the organism being *Bacillus circulans*;

a carrier being inoculated with the spores;

a package for the inoculated carrier, the package including at least a portion having sufficient permeability to admit a sterilizing amount of gas or vapor into contact with the spores, the package being substantially bacteria impermeable; and, an indicator associated with the package and adapted to be visually observed therewith, the indicator changing color from a first color to a different color in response to a fluid component of a sterilizing process, wherein the indicator substantially maintains the first color in the absence of acidic gas or vapor exposure and the different color after acidic gas or vapor exposure is terminated.

18. The packaging system as in claim 17 wherein the sterilizing process component is an acidic gas or vapor.

19. A tape adapted to be affixed to biocontamination barriers for articles to be sterilized by a sterilization cycle including exposure to an acidic fluid, comprising:

an elongated, flexible member having an adhesive layer on one side and a dye composition on the other side, the dye composition being substantially stable and capable of visually indicating whether exposure to an acidic fluid of a sterilization cycle has occurred, the dye composition including a pH sensitive dye and a pH adjusting agent, the pH sensitive dye giving a substantially stable color change in response to acetic fluid exposure, the pH adjusting agent adjusting the pH of the dye composition to between about 4.6 to about 6.5.

20. The tape as in claim 19 wherein the dye composition includes Bromophenol Blue or Bromocresol Green.

21. The tape as in claim 20 wherein the dye composition changes color in response to acetic acid exposure and substantially maintains the changed color after exposure to acetic acid is terminated.

* * * * *